United States Patent [19]

Meloy

[11] Patent Number: 4,519,244

[45] Date of Patent: May 28, 1985

[54] CASECADEOGRAPH AND METHOD OF USE

[76] Inventor: Thomas P. Meloy, 2202 Maple St., Morgantown, W. Va. 26505

[21] Appl. No.: 506,243

[22] Filed: Jun. 21, 1983

[51] Int. Cl.³ .................... G01N 15/00; G01N 33/40; G01N 33/00
[52] U.S. Cl. ............................ 73/432 R; 73/432 PS; 209/237
[58] Field of Search ........... 73/432 R, 432 PS, 432 Z; 209/237, 209, 135

[56] References Cited

U.S. PATENT DOCUMENTS 2,782,926   2/1957   Saxe .................................. 209/237

Primary Examiner—S. Clement Swisher
Attorney, Agent, or Firm—William H. Wright

[57] ABSTRACT

This invention relates generally to the field of particle chromatography, and more specifically to a method and apparatus employing the cascade principle for the purpose of characterizing particles according to subtle differences between the individual particle contours, by passing the particles through a repetitive series of sieves in a column, that have the same mesh size and are dimensioned to pass the entire sample, and wherein the particle characterization is based upon resident time of the similarly shaped particles within the column.

54 Claims, 11 Drawing Figures

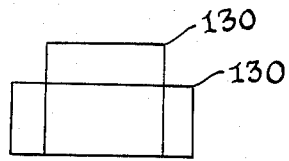
FIG. 5A.
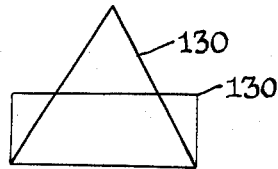
FIG. 5B.
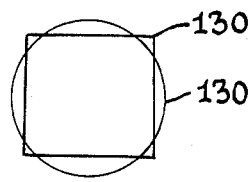
FIG. 5C.
FIG. 6.
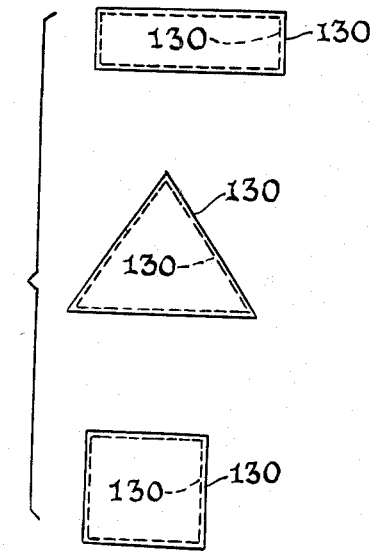
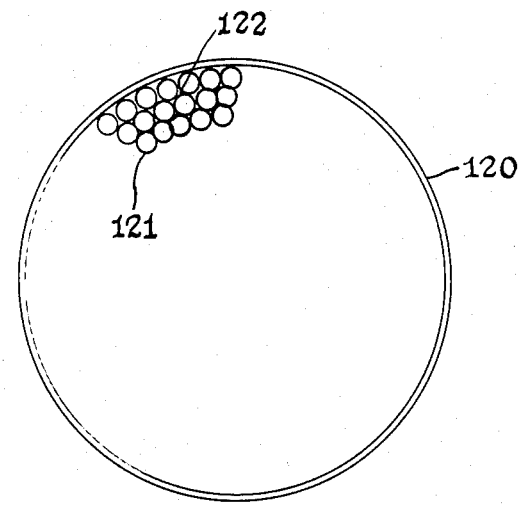
FIG. 7.

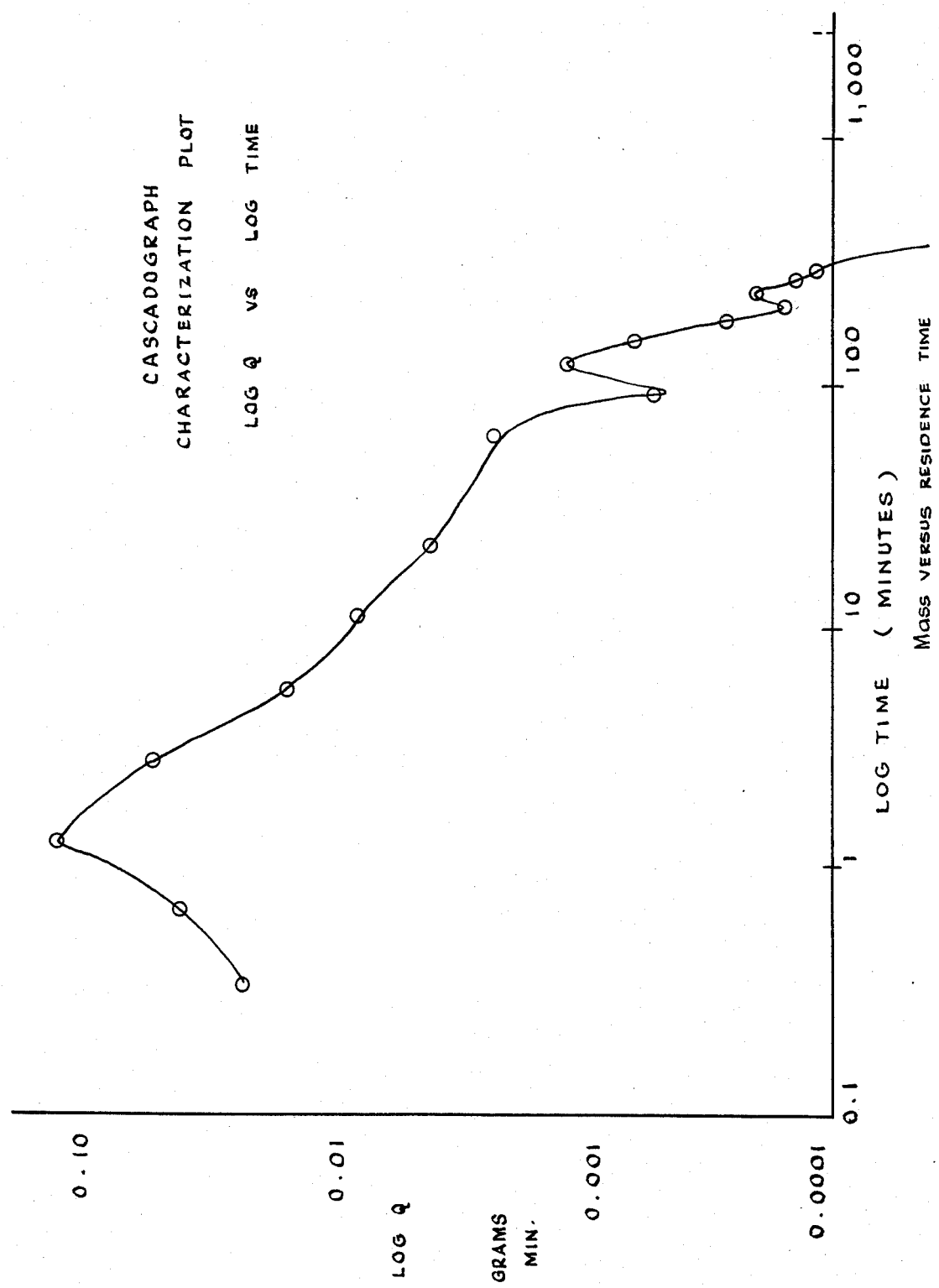

CASECADEOGRAPH AND METHOD OF USE

BACKGROUND OF THE INVENTION

Particle chromatography, called Cascadography, operates in a manner similar to all the chromatographs. The sample is injected, as a pulse, into the system and is immediately carried into a sorption column or stack where the particles move from one "plate" to the next. In moving from "plate" to "plate" the speed is governed by the individual particle's characteristics. After the particles exit the stack, they encounter a detector which measures the particles. A recording is made of the stack output as a function of time. If there exists in the sample a group of particles with identical or very nearly the same characteristics, then the output recording will show a pulse or peak.

The great bulk of material handled in industry is in the particulate or powder form, yet, to date, most of the analytical, research, experimental and development work has been done on fluids. Since fluids are more uniform in nature, far easier to characterize and to analyze, it is not surprising that fluid chromatographs would be in the most advanced state of development. Because of the extraordinary industrial importance of powders, any theoretical or instrumental breakthroughs in the powder field is important from both the scientific and economic viewpoint. Cascadography, because of its ease in characterizing powders, is this type of breakthrough.

Particle characterization has come slowly to the powder field because, unlike molecules, each particle in the universe is unique. Cascadography is a sophisticated concept for the powder field and was developed specifically to characterize powders. A quantitative method, called Fourier Grain Analysis or Morphological Analysis, of measuring the shape of individual particles, has been extended to measuring the shape mix in powders, when it is desired to know if two powders samples are from the same or a different source. For a given size of particle, this method requires that the shape of two hundred particles be measured in each sample and then, using clustering theory in hyperspace, a comparison is made between the two powders to see if there is a significant difference between the two shape mixes to confirm that the powders come from different sources.

While Morphological Analysis is a powerful, sophisticated research technique of great promise, it neither separates the particles into discrete batches, nor does it survey the entire sample. In short, it does not characterize the powder. However, cascadography, like sieving, is both easy to do and easy to understand. By temporally separating particles, Cascadography characterizes powders in a new dimension, residence-time-shape. This form of characterization is immediately applicable to industrial problems as diverse as the grading of grains, wheat and corn, as well as the characterizing of abrasives.

One separation unit operation never successfully modeled is sieving. To successfully model any unit operation, one must know both the characteristics of the feed and the selectivity function of the unit operation. Particles of different shape, even though their "size" is the same, will pass through a sieve at different rates. Yet Jansen et. al. showed that the sieving of mono size spheres obeys an exponential decay law for the number of spheres remaining on a sieve. Obviously the feed for normal size distribution consists not only of variations in particle size, but also of particle shape. As has been shown by Roberts and Beddow, these shape variations effect the rate at which particles progress through the sieve. Until now, no one has either characterized the feed to a sieve, any other sizing device, or even suggested a method for doing so. This invention presents a method, called Sieve Cascadography, and an apparatus called a CASCADEOGRAPH that will characterize the feed to a sieve or industrial screen.

Consider now several unsolved industrial problems, one on grain grading and the other on abrasive evaluation and quality control. Since there are no instrumental methods of grading food grain, it is done by humans, resulting in an expensive, judgemental and corruptible system, as is reported in the press from time to time. Needed is a method to measure the amount of whole grain, cracked grain, filth, chaff and adulterants in a sample. Cracked grain is elongated and smaller than whole grain, chaff is very elongate, rat or mouse boluses are smooth and ellipsoidal, and finally adulterants may have any shape-size. Each of these particles will have their own residence time characteristics on a sieve and thus will report at a different time to the cascadograph product. Just by looking at the output of the cascadograph one can quantitatively tell the ratio of whole to cracked corn, the amount of filth and chaff, and if there is an unusual peak or profile, the amount of adulterant.

In the abrasive industry there are two useful particle shapes, triangles and blocks, in addition, there are useless shapes such as plates. Triangular particles are useful in the making of grinding wheels, while blocky particles are good for grits and abrasive sheets. If one is manufacturing or buying an abrasive one wants to know the particle shape content but at present there is no satisfactory way of profiling the abrasives shape mix. Since each shape particle, for a narrow size range, has a characteristic residence time on a sieve, Sieve Cascadography is an ideal method of assaying the shape profile of an abrasive sample. Both buyer and vendor can agree on the specification and simple tests can be made to determine if the sample meets the specification.

SUMMARY OF THE INVENTION

Cascadography, a form of particle chromatography, is a new, generic method of separating and characterizing mixes of mineral or particle species based on subtle physical differences such as shape, or size. The Cascadograph works on the same principle as a Gas or Liquid Chromatograph. For sieving, or screening, it is a form of shape spectroscopy. Like gas chromatography, cascadography characterizes a sample by the temporal separation of particle species. Using a number of identical sieves in series as the stack, the sample feed is injected into the first sieve at time equals zero, and samples are taken at regular time intervals from the last sieve in the stack. Material moves from one sieve to the next in the stack so that the product from the $i^{th}$ sieve becomes the feed to the $i+1^{st}$ sieve. Other than as a product, no material is removed from any sieve, there is no circulating load or feedback. First to appear in the product are the rapidly moving particles followed by the slower ones. For example, if there exists a number of identical particles, then all those particles will appear at roughly the same time in the output of the system. As the number of sieves in the series increases, so does the resolution between batches of particles with similar properties. If the system being studied is sieving, then regular as well as irregularly shaped particle's sieving rates can be assayed for the feed and waste streams, and from this information, the sieve selectivity function can be calculated.

Consider now a simple system of n, identical sieves all having the same mesh size. In practice, the rate at which particles move through such a stack of sieves depends on the shape and size of the particles. Gas Chromatography is analogous to the Sieve Cascadograph characterization system. Since a very close analogy exists between gas chromatography and cascadography, one may compare the physical constants of the two systems. For a gas, the residence time on the wall (i.e., half life) governs the time until that species appears in the product, and is analogous to the residence time (half life) that a particle spends on a given screen. A good measure of the ability of the gas chromatograph to resolve two chemical species with closely related absorption times is the length to diameter, L/D, ratio of the gas chromograph tube. In a similar manner for screening, the greater the number of sieves in the cascade, the better the separation between minerals with comparable residence times.

In the case of Sieve Cascadography, particles remain on a sieve and then pass through that one to the next sieve. A sieve Cascadograph consists of n, identical size screens in a stack. For example, a 20 stack, 100 mesh cascadograph is a stack of 20, 100 mesh sieves, one on top of the other with a pan in the bottom, just like a regular screen stack used for size analysis. The sample is placed on the top sieve and sieving begun. Currently, at preset time intervals, the pan fraction is removed, weighed and examined under a microscope for shape changes. Each particle has a characteristic time that it spends on each of the identical sieves. Particles with short residence times will pass through the sieve above, remain for a short time on the new sieve, and then pass through that sieve to the one below. Each particle must pass through the same number of sieves before it leaves the cascadograph. Particles with short residence times on a sieve will be the first to appear in the stack's output followed by the slower moving particles with the longer residence times.

In Sieve Cascadography, one is trying to find the weight of material of a given residence time and sieve size that is in the feed or product of a sizing operation. For a given sieve, each particle has a specific residence time (half life). For that particle to pass through n, identical sieves, it must spend time on each screen. For each particle, the time spent on any one sieve is exponentially distributed. To compute the total time of a given particle on the n sieves, one samples an exponential frequency distribution n times. The Gausian sampling theorum states, that as n goes to infinity, the sum of these n residence-time samples will become Gausian distributed and the mean of the sum will equal n times the mean of the exponential frequency distribution of residence-time on one of the sieves. This means that if one plots the mass flow, Q, from the last sieve in the stack as a function of the log of time, and if the sample contains several batches of particles of the same size and shape, then one will obtain a plot with a series of peaks and valleys, just as one would expect in gas chromatography. A peak would represent the mass due to a number of particles having the same residence time on a sieve. Thus, this new system is residence time spectroscopy. Since the shape is closely correlated with particle residence time on a sieve, cascadography can be used to measure the shape profile in a powder, a form of shape spectroscopy. Because cascadography separates particles, it also can be used to separate particles based on their sieve residence times.

OBJECTS OF THE INVENTION

An object of the present invention is the development of a new method for characterizing dry particles based on subtle differences in the respective particles shapes and contours.

Another object of the present invention is the development of a technique of particle analysis that will lend itself to a variety of industrial applications.

Yet another object of the present invention is to provide a technique of particle analysis, that uses a series of multiple elements having uniform openings to measure the residence time of individual particles passing through the multiple elements.

Still another object of the present invention is to provide a technique of particle analysis, that uses a series of multiple elements having a uniform mix of openings within a narrow size range to measure the residence time of individual particles during their passage through the multiple elements.

A further object of the present invention is to provide a method a particle analysis that may be used for particle sizes of one micrometer and above.

A still further object of the present invention is to develop a method of particle analysis employing sequential beds of packed microspheres having a uniform diameter to impede the passage of particles through the interstices between the microspheres in each of the beds.

Yet another object of the present invention is the development of a sieve cascadograph used to practice the technique of cascadography, which is a form of particle chromatography.

These and other objects, advantages, and novel features of the method and apparatus will become apparent from the detailed description that follows, when considered in conjunction with the accompanying drawings.

BRIEF DESCRIPTION OF THE INVENTION

FIGS. 5A, 5B and 5C illustrate that differently configured mesh openings can have the same size.

FIG. 6, illustrates mesh openings having the same configuration but slightly different sizes.

FIG. 7, shows another form of the repetitive elements employed in the apparatus.

FIG. 8 is a graphical representation of a mass versus residence time characterization plot.

DETAILED DESCRIPTION OF THE PREFERRED EMBODIMENT

Prior to describing the method and apparatus that form the basis of this invention, it is to be understood that the invention relates to the analysis and separation of a narrow size range of constituent particles in a powder, wherein powder includes, but is not limited to, naturally occurring and manufactured powders such as abrasives and comminuted material, food grains such as wheat and corn, and naturally occurring materials such as sand and soils.

It should also be appreciated that the term size range as defined by the largest and smallest of the constituent particles in any powder subject to analysis can be extremely broad in some instances, yet narrow in the instance of fine powders. In the first instance mentioned only a portion of the powder would fall into the narrow size range, whereas in the latter instance, the entire volume of powder could be encompassed by the Δ selected size range.

In both of the aforementioned instances only a sample of the constituent particles are passed through the apparatus, and that sample preferably contains only a limited number x of the particles that fall within the given size range, for reasons that will be explained in greater detail further on in the specification.

Figure 1:
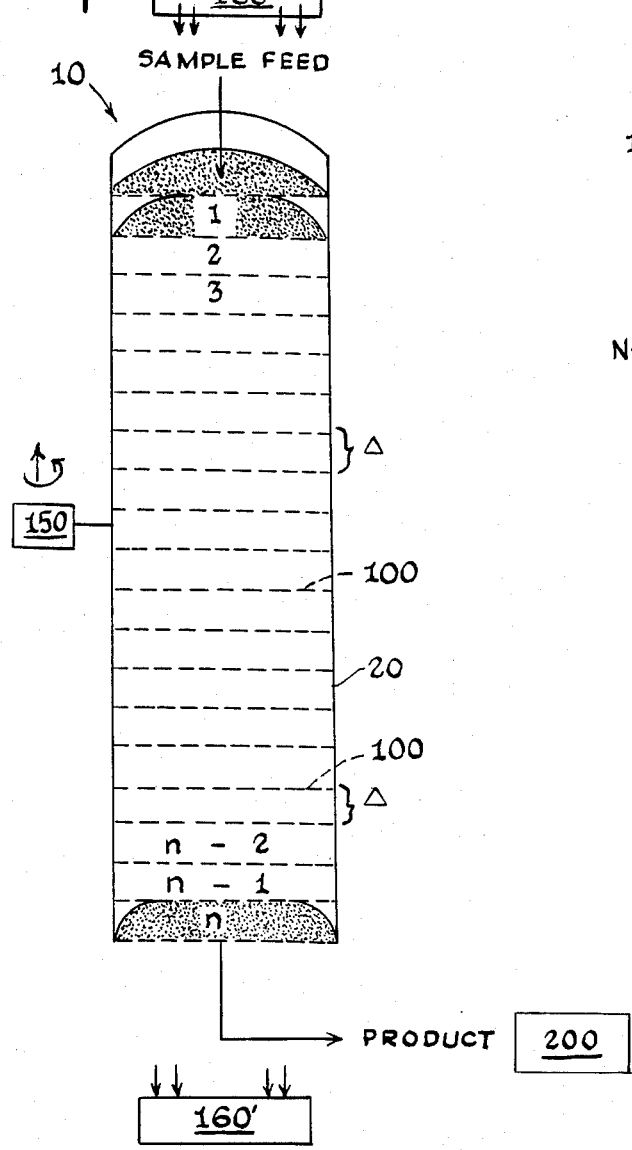
FIG. 1, is a perspective view of the apparatus that is used to practice the method of this invention.

As can best be seen by reference to FIG. 1, the cascadeograph that forms the structure required to practice the method of the invention is designated generally as 10, and comprises a vertically disposed elongated column 20 having a number n of repetitive elements 100 horizontally disposed across the interior of the column 20 at spaced intervals.

Figure 2A:
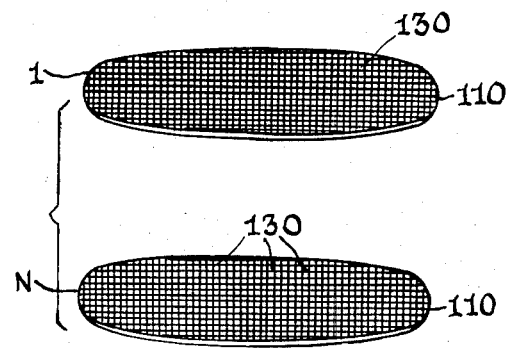
FIG. 2, shows one form of the repetitive elements employed in the apparatus.
Figure 2B:
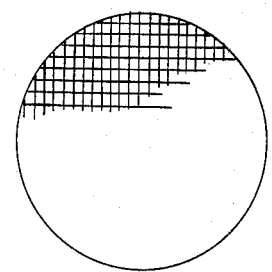
Figure 3:
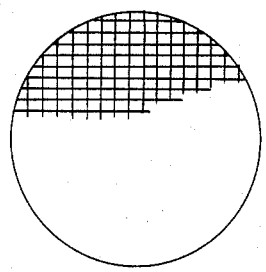
FIGS. 3 and 4, show the various mesh opening configurations that may be employed in the repetitive elements.
Figure 4:
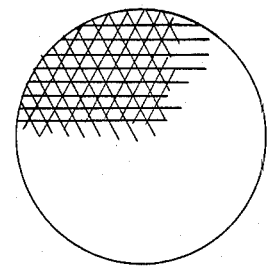

In one form of the preferred embodiment illustrated in FIG. 2, each of the repetitive elements 100 comprises a sieve 110 having openings 130 formed therein. While each sieve 110 is provided with a uniform array of openings 130, the geometric configuration of the openings may vary from sieve to sieve as shown in FIGS. 3 and 4. In addition, the openings 130, while having different geometric configurations such as the square, rectangular, and triangular shapes shown, may also have the same size opening as illustrated in FIG. 5 a through b. Furthermore the sieve openings 130 in each sieve may have openings that share the same geometric configuration; however, the size of the openings may vary over a very limited range, as will be explained further on in the specification (see FIG. 6).

In another form of the preferred embodiment illustrated in FIG. 7, each of the repetitive elements 100 comprises a packed bed 120 of objects 121, wherein the interstices between the objects from a uniform array of openings 130. The objects 121 chosen for the repetitive elements 100 are monospheres 122. While the monospheres within each packed bed must have identical diameters, the monospheres within different beds may have diameters that vary over an extremely limited size range.

The openings 130 in each of the repetitive elements as heretofore described may fall into the following categories: (a) all of the openings have the same size and shape; (b) the openings have the same size but different shapes; (c) the openings have the same shapes but a very limited size range; and (d) the openings have different shapes and a limited size range.

It is also to be understood that, for the purposes of this specification, the term repetitive elements may represent identical elements, identical series of elements, or identical groups of different elements.

The method that is practiced by using the aforementioned structure comprises the following general steps; sizing of the constituent particles of a powder within a narrow size range; selection of a limited number of sized particles to form a sample; feeding the sample through the apparatus; and detecting the residence time of similarly shaped particles during their passage through the apparatus.

The first step in the method requires that a narrow size range of particles be removed from the volume of powder to be analyzed. To begin with, particles both above and below the size range must be removed from the powder. Obviously, since the entire sample must pass through the apparatus, the oversized particles must be removed, as well as the undersized particles, that would pass too rapidly through the apparatus to provide any meaningful results. The particular technique that is employed in the sizing operation may comprise; sieving or acoustical, optical, electrical or other particle size classification techniques. It is only necessary for the purposes of this invention that a portion of the constituent particles having a narrow size range be separated from the powder.

From this portion of the sized particles, a limited number x of particles are removed to from the sample that will be fed into the apparatus. The sample is deposited on the first of the n repetitive elements at time equals zero and the entire sample will have passed through the $n^{th}$ repetitive element after a period of time has elapsed. Ideally, the sample should pass through the apparatus solely by gravitational forces; however, as a practical matter an intermittently induced force must be applied, to re-orient the individual particles residing on different repetitive elements so that the particles can pass through the openings and move from one repetitive element to the next.

In one form of the preferred embodiment, the intermittently induced force has both a vertical and horizontal component which is produced by a vibration imparting mechanism 150 that is operatively connected to the apparatus to apply a force that is uniformly distributed among the repetitive elements. It should be noted that this vibration imparting mechanism is employed primarily when the repetitive elements comprise the sieves mentioned supra.

In another form of the preferred embodiment the intermittently induced force is pulsating in nature and is transmitted through the apparatus in the direction of travel of the sample. It should be noted that this pulsating force is employed primarily when the repetitive elements comprise the packed beds of monospheres mentioned supra; and would normally be produced by a pressure pulse introduced into the column by any one of a number of positive 160 or negative 160' pressure inducing means (shown in phantom) operatively associated with one of the column openings.

Heretofore, the openings 130 in the repetitive elements 110 and 120 have been described in terms of their size, shape, and the physical structure that created them. The specification will now deal with an equally important aspect of the invention, i.e., the relationship of the number $y_{1 \text{ through } n}$ of the openings in each repetitive element and the number x of particles in the sample.

Experimentation has proven that the major impediment to the passage of the entire sample through the apparatus has been the "blinding" or "poisoning" of the first element in the column due to the particle to particle interference that results from more than one particle converging on the same opening on a given repetitive element. Obviously this situation is particularly critical for the first repetitive element, since this element is the only element that receives the entire sample virtually simultaneously.

In order to minimize the particle to particle interference experienced by the first repetitive element, the sample theoretically comprises a number x of particles, that is approximately equal to, but less than, the number $y_2$ of openings in the first repetitive element. Since the number $y_2$ of openings is known, and the average weight of the particles in the given size range can be determined; the sample is chosen by removing a given weight from the sized particles that should correspond to a number x of particles, wherein the value of x is only minimally less than the value of $y_2$.

In the preferred embodiment, the number of openings $y_{1\ through\ n}$ of the repetitive elements should have a constant value. However, due to the differences in constructing elements having different shape and size openings, the value of y may be different; among individual elements having different shaped openings; and among individual elements having the same shape, but different sized openings. Even though the values of $y_{1\ through\ n}$ may vary, the range of values will be kept as narrow as manufacturing tolerences will permit.

As shown in FIG. 1, the column 20 is provided with n repetitive elements spaced a distance Δ apart. As with any analytical method the larger the value of n the more refined the results, and ideally the maximum value of n would equal ∞. As a practical matter, however, this invention is only concerned with the minimum value of n, which in the preferred embodiment is never less than ten. Again for practical considerations, the interval Δ would normally be chosen to accomodate the largest number n of repetitive elements within a column of a given length. However, in this particular instance the average length of the longest particles in the sample will be determinative of the value of Δ.

Given the fact that the longest particles must be aligned along their longitudinal axis, in order to pass through any of the openings 130 in the repetitive elements; and the openings in successive elements will not necessarily be aligned, the minimum value of Δ will be approximately equal to the average length of the longest particles in the sample. In addition, depending on the particular powder being analyzed, the value of Δ can be as much as two to four times the width of the average opening 130 in the column.

As was mentioned supra the method and apparatus that form the present invention were developed to analyze a narrow size range of constituent particles, in what has been loosely defined as a powder. The reason that the size of the openings in the repetitive elements, and the size range of the particles, has not been set forth in the specification, is due to the fact that the openings 130 can be sized to analyze narrow ranges of particles, whose average particle size can vary from one or more centimeters down to the micrometer level.

As shown in FIG. 1, a detector 200 is disposed at tne output end of the column to analyze and plot the product versus time, as the individual particles exit from the $n^{th}$ repetitive element. Since no two particles are exactly the same in size, shape and contour, each particle will have its own unique residence time within the column. However, particles having similar shapes and contours will have similar residence times within the column.

A typical plot of the output of the column 20 as sensed by the detector 200 is reproduced in FIG. 8. The typical mass versus time curve will characteristically produce a curved line having a series of peaks. Observation of the physical properties of the individual particles versus time shows that spherical, rounded and smooth particles will be the first to appear in the product, followed by generally uniform sized particles having irregular surfaces, and finally elongated particles with irregular surfaces. Each group of similarly shaped particles will produce its own unique peak, and the number of individual peaks produced will be increased by increasing the number n of repetitive elements employed in the column.

Again the specific type of detector 200, chosen to analyze and plot the output of the column 20, is not considered to form a part of this invention, and the detector may be in the form of any suitable mechanical, electrical, acoustical or optical apparatus that is capable of sensing and recording the output of the column over a period of time.

It should be noted at this juncture, that since the invention broadly teaches the pre-sizing of the particles from which the sample is taken; that this teaching could also be extended to particles within the sample, that exit from the apparatus within a given increment of time by virtue of their similarity in shape and contour; and that the method could be repeated again to further characterize those similarly shaped particles.

Having thereby described the subject matter of this invention, it should be obvious that many substitutions, modifications, and variations of the invention are possible in light of the above teachings. It is therefore to be understood that the invention as taught and described is only to be limited to the extent of the breadth and scope of the appended claims.

What I claim is:

1. A method of separating and analyzing powders by virtue of their constituent particles having a pre-selected size range, comprising the steps of
    (a) separating at least a portion of the particles having the pre-selected size range from the powder
    (b) creating a sample from a number x of the separated particles
    (c) passing the entire sample over a period of time through a number n of repetitive elements having a number $y_{1\ through\ n}$ openings, wherein the maximum value of x is less than the minimum value of y
    (d) determining the residence time, of the particles in the sample having similar shapes, during their passage through the n repetitive elements.

2. A method as in claim 1, further comprising the step of
    (e) analyzing the particles that emerge from the repetitive elements during a given increment of time.

3. A method as in claim 2, further comprising the step of
    (f) passing the particles of step (e) through a plurality of repetitive elements that are identical in construction, and repeating step (d).

4. A method as in claim 1, wherein the repetitive elements of step (c) are identical in construction.

5. A method as in claim 1, wherein groups of the repetitive elements of step (c) are different in construction.

6. A method as in claim 1, wherein the repetitive elements of step (c) comprise individual sieve elements.

7. A method as in claim 6, wherein the openings in each individual sieve element are uniform in size and configuration.

8. A method as in claim 7, wherein the size and configuration of the openings in each individual sieve element is identical.

9. A method as in claim 7, wherein the size and configuration of the openings among groups of sieve elements are different.

10. A method as in claim 1, wherein the repetitive elements of step (c) comprise individual packed beds of monospheres.

11. A method as in claim 10, wherein all of the monospheres have the same diameter.

12. A method as in claim 10, wherein the diameters of the monospheres among groups of packed beds are different.

13. A method as in claim 1, wherein the repetitive elements of step (c) comprise packed beds of spherical objects.

14. A method as in claim 1, wherein the repetitive elements of step (c) comprise packed beds of non-spherical objects.

15. A method as in claim 1, wherein the repetitive elements of step (c) comprise packed beds of mixed spherical and non-spherical objects.

16. A method as in claim 1; wherein the sample is passed through the repetitive elements by gravitational forces.

17. A method as in claim 1; wherein the sample is passed through the repetitive elements by gravity and intermittently induced forces.

18. A method as in claim 17, wherein the intermittently induced forces have a vertical and horizontal component.

19. A method as in claim 17, wherein the intermittently induced forces are pulsed.

20. A method as in claim 17, wherein the intermittently induced forces are applied uniformly among the repetitive elements.

21. A method as in claim 17, wherein the intermittently induced forces are applied unevenly among the repetitive elements.

22. A method as in claim 1, wherein the given number n of repetitive elements is a whole number having a value of at least the number ten.

23. A method as in claim 3, wherein the given number n of repetitive elements and the said plurality of repetitive elements are equal.

24. A method as in claim 3, wherein the given number n of repetitive elements and the said plurality of repetitive elements are unequal.

25. A method as in claim 4, wherein the given number n of repetitive elements and the said plurality of repetitive elements are equal.

26. A method as in claim 1, wherein the given number n of repetitive elements and the said plurality of repetitive elements are unequal.

27. An apparatus used to separate and analyze by shape and contour a particle sample containing a narrow size range of a number x of constituent particles of a powder comprising:
an elongated column, and
a number n of repetitive elements horizontally disposed across the interior of the column at spaced intervals, wherein each of the repetitive elements is provided with a number of $y_{1\ through\ n}$ of openings that will allow the entire sample to pass through the column, and wherein the maximum value of x is less than the minimum value of y.

28. An apparatus as in claim 27, further comprising intermittent force producing means associated with the column for assisting the passage of the sample through the openings in the repetitive elements.

29. An apparatus as in claim 28, wherein each of the repetitive elements are provided with uniform openings.

30. An apparatus as in claim 29, wherein all of the openings have the same size and shape.

31. An apparatus as in claim 30; wherein the value of y for each of each repetitive element is the same.

32. An apparatus as in claim 28, wherein the intermittent force producing means imparts a force to the repetitive elements that has a component in both the horizontal and vertical plane.

33. An apparatus as in claim 32, wherein the horizontal component displaces the repetitive elements a distance of approximately twice the average width of the particles in the sample.

34. An apparatus as in claim 28, wherein the intermittent force producing means imparts a pulse through the column in the direction of the particle flow.

35. An apparatus as in claim 29, wherein the openings in different repetitive elements have the same size but different geometric shapes.

36. An apparatus as in claim 29, wherein the openings in different repetitive elements have the same geometric shape but different sizes.

37. An apparatus as in claim 29, wherein the number of openings in any repetitive element is greater than the limited number of particles in the sample.

38. An apparatus as in claim 27; wherein the number "n" is at least equal to the number ten.

39. An apparatus as in claim 27; wherein the interval is uniform.

40. An apparatus as in claim 39; wherein the minimum length of the interval is approximately equal to, but less than, the length of the longest particle in the sample.

41. An apparatus as in claim 27 further comprising a detection means operatively disposed at the output end of the column to monitor the residence time of similarly shaped particles as the sample passes through the column.

42. An apparatus as in claim 27, wherein the repetitive elements comprise sieves.

43. An apparatus as in claim 27, wherein the repetitive elements comprise packed beds of monospheres.

44. An apparatus as in claim 27, wherein the repetitive elements comprise packed beds of non-spherical objects.

45. A method of analyzing powders by virtue of their constituent particles having a pre-selected size range, comprising the steps of
(a) separating at least a portion of the particles having the said pre-selected size range from the powder;
(b) creating a sample through a number x of the separate particles;
(c) passing the sample through a number of identical unit operations;
(d) detecting the output of each unit operation over a period of time, and
(e) plotting the output of each unit operation over time to provide a characterization of the constituent particles based on their residence times through each unit operation.

46. A method as in claim 45, wherein steps (a) through (e) are used to practice a form of particle chromatography.

47. A method as in claim 46, wherein a gas is used to transport the sample through the said unit operations.

48. A method as in claim 46, wherein a liquid is used to transport the sample through the said unit operations.

49. A method as in claim 46, wherein steps (a) through (e) are used to characterize the constituent particles of the sample via a form of shape spectroscopy.

50. An apparatus used to characterize a particle sample containing a narrow size range of a number x of constituent particles of a powder, wherein the apparatus comprises:
   an elongated column, and
   a number n of repetitive elements disposed across the interior of the column at spaced intervals, wherein each of the repetitive elements are provided with a number $Y_{1\ through\ n}$ of openings that will allow the entire sample to flow through the column.

51. A method characterizing a powder sample, comprising the steps of
   (a) passing the powder sample through repetitive unit operations;
   (b) sensing and recording the output values for each of the repetitive operations, and
   (c) plotting the output versus time values for at least one of the repetitive operations.

52. An apparatus an in claim 50 wherein each of the repetitive elements comprises
   individual, removable sieves stacked together and disposed within the said column, wherein adjacent sieves are spaced from one another a distance $\Delta$ apart.

53. An apparatus as in claim 52 wherein the minimum value of $\Delta$ is less than the average length of the longest particles in the said particle sample.

54. An apparatus as in claim 52, wherein the value of $\Delta$ is approximately equal to, but less than, the average length of the longest particles in the said particle sample.

* * * * *